(12) United States Patent
Lalena et al.

(10) Patent No.: US 10,629,000 B2
(45) Date of Patent: *Apr. 21, 2020

(54) SYSTEM PROVIDING COMPANION IMAGES

(71) Applicant: CARESTREAM HEALTH, INC., Rochester, NY (US)

(72) Inventors: Michael C. Lalena, Webster, NY (US); Kevin C. Odorczyk, Rochester, NY (US); Xiaohui Wang, Pittsford, NY (US); Karl F. Hoeflein, North Chili, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/003,423

(22) Filed: Jun. 8, 2018

(65) Prior Publication Data

US 2018/0293794 A1 Oct. 11, 2018

Related U.S. Application Data

(63) Continuation of application No. 12/942,270, filed on Nov. 9, 2010, now Pat. No. 9,996,971.

(60) Provisional application No. 61/264,271, filed on Nov. 25, 2009.

(51) Int. Cl.
*G06F 3/048* (2013.01)
*G06T 19/00* (2011.01)
*G06F 19/00* (2018.01)
*G16H 30/20* (2018.01)
*G16H 30/40* (2018.01)

(52) U.S. Cl.
CPC ............. *G06T 19/00* (2013.01); *G06F 3/048* (2013.01); *G06F 19/00* (2013.01); *G06F 19/321* (2013.01); *G16H 30/20* (2018.01); *G16H 30/40* (2018.01)

(58) Field of Classification Search
CPC ............................... G06F 3/048; G06T 19/00
See application file for complete search history.

(56) References Cited

U.S. PATENT DOCUMENTS

| | | | |
|---|---|---|---|
| 5,079,698 A | 1/1992 | Grenier et al. |
| 5,235,510 A | 8/1993 | Yamada et al. |
| 5,668,888 A | 9/1997 | Doi et al. |
| 6,628,815 B2 | 9/2003 | Wang |
| 6,985,555 B2 | 1/2006 | Endo |

(Continued)

OTHER PUBLICATIONS

NPL—as provided by the Examiner for U.S. Appl. No. 12/942,270, dated Feb. 5, 2018, 2 pages.

*Primary Examiner* — Xuyang Xia

(57) ABSTRACT

A method for presenting radiographic images of a subject obtains, from the same radiographic image capture, at least a first image and a second image, wherein the at least first and second images differ in presentation. The method associates the at least first and second images as companion images according to one or more entered instructions. There is displayed at least a first executable data link that relates to a first storage location of the first image and a second executable data link that relates to a second storage location of the second image. In response to an operator selection of either of or both of the first and second executable data links, the method displays either the corresponding first or second image, or both companion images.

20 Claims, 21 Drawing Sheets

(56) References Cited

U.S. PATENT DOCUMENTS

| | | |
|---|---|---|
| 7,130,457 B2 | 10/2006 | Kaufman et al. |
| 2001/0040992 A1 | 11/2001 | Foos et al. |
| 2003/0164860 A1 | 9/2003 | Shen et al. |
| 2004/0008900 A1 | 1/2004 | Jabri et al. |
| 2005/0038678 A1* | 2/2005 | Qian ................. A61B 5/00 705/2 |
| 2008/0025583 A1 | 1/2008 | Jabri et al. |
| 2008/0152204 A1* | 6/2008 | Huo .................. G06K 9/2054 382/132 |
| 2009/0003679 A1* | 1/2009 | Ni ..................... A61B 6/025 382/132 |
| 2009/0021475 A1 | 1/2009 | Steinle et al. |
| 2009/0190818 A1 | 7/2009 | Huo |
| 2009/0192823 A1 | 7/2009 | Hawkins et al. |
| 2009/0274384 A1* | 11/2009 | Jakobovits .......... G06F 16/51 382/254 |
| 2010/0098314 A1 | 4/2010 | Huo et al. |

\* cited by examiner

SYSTEM PROVIDING COMPANION IMAGES

CROSS REFERENCE TO RELATED APPLICATIONS

This application is a Continuation of U.S. Ser. No. 12/942,270 filed on Nov. 9, 2010, entitled "SYSTEM PROVIDING COMPANION IMAGES", in the names of Lalena et al, which granted on Jun. 12, 2018 as U.S. Pat. No. 9,996,971, which claims priority from Provisional U.S. Patent Application Ser. No. 61/264,271, entitled "COMPANION IMAGES" by Lalena et al., filed Nov. 25, 2009; both disclosures of which are incorporated by reference in this application.

FIELD OF THE INVENTION

The invention relates generally to the field of radiographic imaging, and more particularly to a system for management and display of companion images for various types of radiographic images, including medical images.

BACKGROUND OF THE INVENTION

The capability to provide a radiographic image in digital form makes it possible to apply a range of image processing utilities and applications. This includes applications for improving image appearance and for presenting and highlighting or accentuating various features within the image, including features of both clinical and diagnostic significance for medical images. Thus, for example, an original digital image for a chest x-ray can be processed not only to help assist in detection and diagnosis of a patient's condition, but also to help improve the detectability of a tube or a PICC (Peripherally Inserted Central Catheter) used during medical procedures. Advantageously, a single exposure of the patient to x-ray radiation can provide primary, original image data for processing in any number of ways to generate multiple processed images, each designed to help to show particular features.

There are various image processing utilities available, depending on the type of medical image that is obtained. For a chest x-ray, for example, image processing routines have been developed for accentuating tube and tip placement, so that these devices, when inserted into the patient, can be more readily detected. Tube and tip placement detection and highlighting is described, for example, in commonly assigned U.S. Patent Application Publication No. 2010/0098314 entitled "Tube Detection in Diagnostic Images" by Huo et al., and in commonly assigned U.S. Patent Application Publication No. 2009/0190818 entitled "Computer-Aided Tubing Detection" by Huo. Other image processing utilities provide improvements in image contrast which can be applied over one or more regions of interest or globally, rib suppression to help improve visibility of lung tissues, and processing treatments that help in the detection of pneumothorax or other conditions.

In addition to images having particular processing utilities applied, it can be generally beneficial to associate images for a patient so that, for example, comparison of images obtained at different times can be performed.

SUMMARY OF THE INVENTION

An object of the present invention is to address the need for presenting companion images in a usable format for clinical and diagnostic uses.

Another object of the present invention is to provide utilities for management and use of companion images and for their association with the original or primary image.

A further object of the present invention is to coordinate operator markup and editing of a primary image with its associated companion images.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for presenting radiographic images of a subject, the method executed at least in part on a computer system and comprising: obtaining, from the same radiographic image capture, at least a first image and a second image, wherein the at least first and second images differ in presentation; associating the at least first and second images as companion images according to one or more entered instructions; displaying at least a first executable data link that relates to a first storage location of the first image and a second executable data link that relates to a second storage location of the second image; and responding to an operator selection of either of or both of the first and second executable data links by displaying either the corresponding first or second image, or by displaying both companion images.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 5 is a plan view of a display screen showing thumbnail symbols where primary and secondary images are available for a patient.

FIG. 7 is a plan view of a display screen used for setting up associations for each of a number of image types.

FIG. 8 is a plan view of a display screen used for displaying information fields in the listing of companion image types.

DETAILED DESCRIPTION OF THE INVENTION

Figure 1:
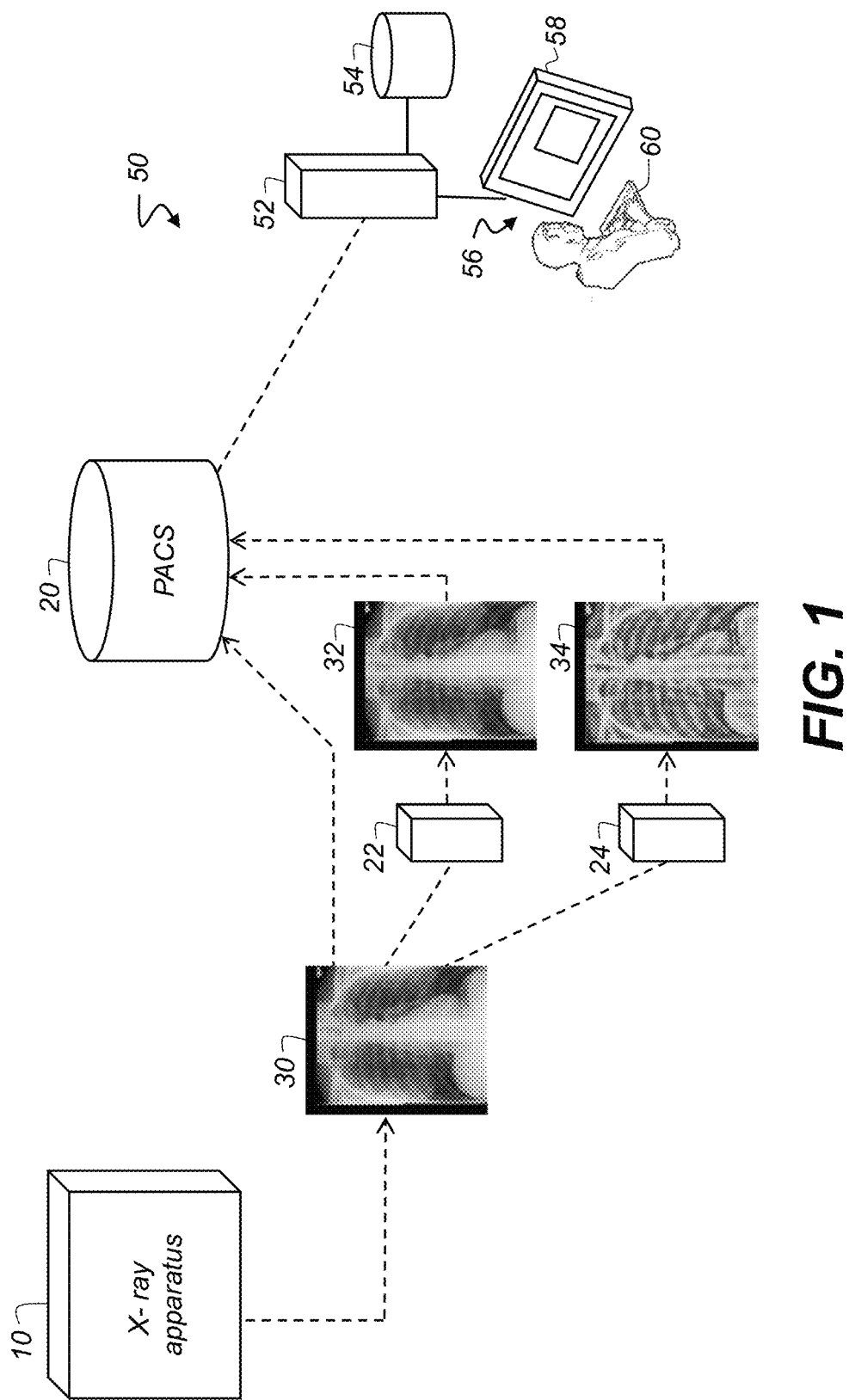
FIG. 1 is a schematic block diagram that shows a system for medical image management.

The following is a detailed description of the preferred embodiments of the invention, reference being made to the drawings in which the same reference numerals identify the same elements of structure in each of the several figures.

As will be appreciated by one skilled in the art, the present invention may be embodied as a system, method, or computer program product. Accordingly, an embodiment of the present invention may be in the form of an entirely hardware embodiment, an entirely software embodiment (including firmware, resident software, micro-code, and other suitable encodings) or an embodiment combining software and hardware aspects that may all generally be referred to herein as a "circuit" or "system." Furthermore, the present invention may take the form of a computer program product embodied in a computer-readable storage medium, with instructions executed by one or more computers or host processors. This medium may comprise, for example: magnetic storage media such as a magnetic disk (such as a hard drive or a floppy disk) or magnetic tape; optical storage media such as an optical disc, optical tape, or machine readable bar code; solid state electronic storage devices such as solid state hard drives, random access memory (RAM), or read only memory (ROM); or any other physical device or medium employed to store a computer program. The computer program for performing the method of the present invention may also be stored on computer readable storage medium that is connected to a host processor by way of the internet or other communication medium.

Those skilled in the art will readily recognize that the equivalent of such a computer program product may also be constructed in hardware. The computer-usable or computer-readable medium could even be paper or another suitable medium upon which executable instructions are printed, as the instructions can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport computer instructions for use by, or in connection with, an instruction execution system, apparatus, or device.

In the context of the present disclosure, the use of terms such as "first", "second", "third", etc., does not by itself connote any priority, precedence, or order of a component or claim element over another or the temporal order in which acts of a method are performed. These terms may be used more generally as labels to distinguish one element having a certain name from another element having the same name (but for use of the ordinal term) or to distinguish the claim elements.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

It should be noted that while the present description and examples are primarily directed to radiographic medical imaging of a human or other subject, the apparatus and methods of the present invention can also be applied to other radiographic imaging applications. This includes applications such as non-destructive testing (NDT), for which radiographic images may be obtained and provided with different processing treatments in order to accentuate different features of the imaged subject.

In the context of the present disclosure, an original or primary image of a subject that is acquired by the system of the present invention may consist of raw image data or may be image data that is automatically pre-processed by the x-ray system itself (so that the raw data is not directly available to users of the system). This is termed the "primary", "original", or "acquired" image of the subject and may include image data from scanned film, from a computed radiography (CR) imaging system, or from a digital radiography (DR) system, for example. An image that has been processed for tube detection, PICC (Peripherally Inserted Central Catheter) detection, contrast improvement, pneumothorax detection, or has undergone other enhancement or processing for enhanced presentation is termed a "secondary" image. The secondary image can be derived from the primary image, wherein the primary image is either raw or pre-processed image data. Alternately, the secondary image and primary image may both be derived from the same source image data, such as raw image data.

The processing of images for functions such as tube and tip detection, PICC detection, contrast improvement, and other functions takes time and requires computer resources. In various environments, different processing functions are executed on different computer systems, so that, for example, a processing module that performs tube and tip enhancement may operate on a single networked workstation and serve multiple x-ray imaging apparatus at a particular site. Thus, even though processed images can be re-generated when they are needed, saving the processed results, short- or long-term, can be advantageous. This can be particularly applicable where decisions are made based on processed images, helping to facilitate later review, for example.

It can be beneficial to store an original image along with any processed "secondary" image that was generated from the same image data. The capability to view both original and processed companion images can help the diagnostician to more clearly identify a condition or to focus on an area of interest in the image. Conventional solutions for image storage and retrieval and for association of multiple images obtained for the same patient employ the PACS (Picture Archiving and Communication System) and various conventional database tools. However, it can be difficult to manipulate conventional systems for obtaining multiple companion images in a readily usable and easily referenced form. Instead, considerable effort and systems expertise is often needed from the technician or diagnostician in order to prepare, store, and retrieve image data for multiple companion images so that it can be suitably presented in a manner that allows a smooth workflow and serves patient needs effectively.

The term "companion" image describes the relation between any two images that are obtained from, or based on, the same radiographic image capture. Considered from a set theory perspective, the primary image and one or more secondary images that are generated as a result of a single image capture form members of a set. Each image in the set is considered to be a companion image relative to any of the other images in the set. Thus, for example, where there is a set of two member images from the same image capture, that is, a primary and a secondary image, both images are considered to be companion images. Where the set has three members, a primary and two secondary images, each member image is considered to be a companion image with respect to that set. In embodiments of the present invention, a single image capture can be used to generate any number of companion images. Relative to the other companion images, each companion image in the set of images has a different presentation, that is, a different appearance, based on how particular image attributes may or may not be enhanced.

Embodiments of the present invention provide a system for management and display of companion images that are derived from the same image capture. The system of the present invention provides an association between two or more companion images and provides tools for management of that association.

As noted, a tube and/or a PICC (Peripherally Inserted Central Catheter) can be employed during medical procedures. There are various types of tubing that could be used. Examples include an endotracheal tube (a breathing tube inserted through the mouth into the trachea); an enteral feeding tube (a feeding tube that ends in the stomach); a nasogastric feeding tube (a tube passed through the nares, down the esophagus and into the stomach); and a gastric feeding tube (a tube inserted through a small incision in the abdomen into the stomach). A PICC is a catheter inserted into a vein and then advanced through increasingly larger veins until the tip rests in the distal superior vena cava or cavo-atrial junction. X-ray images are typically required to verify PICC line placement as well as placement for other tubing and devices.

The schematic diagram of FIG. 1 shows the relationship of companion primary and secondary images and shows the overall relationship of the system of an embodiment of the present invention to a conventional x-ray imaging apparatus 10 and PACS 20. As noted previously, a primary image 30 that is obtained from an image capture by an x-ray imaging apparatus 10 may be provided as either raw or pre-processed image data. Primary image 30 is provided as image data to one or more logic processors 22, 24 that each perform some type of image processing and analysis operation. Each logic processor 22, 24 processes primary image 30 data and generates a companion secondary image 32, 34. In one embodiment, for example, logic processor 22 executes stored instructions to perform tube and line detection and enhancement and generates secondary image 32 that is conditioned by this processing; logic processor 24 executes stored instructions to perform contrast enhancement and generates secondary image 34 as another companion image with its contrast suitably adjusted. Companion secondary images 32 and 34 are stored in the PACS 20 along with acquired primary image 30, which is also considered to be a companion image. It should be noted that logic processors 22 and 24 are representative of one embodiment; in another embodiment, the same computer system functionally provides multiple processors for generating companion secondary images 32 and 34. It should also be noted that, although two secondary images are shown in FIG. 1, one, two, or any number of companion secondary images 32 and 34 can be generated from primary image 30.

The embodiment of FIG. 1 suggests that primary image 30 is pre-processed and suitable for storage/archival as it is provided from x-ray imaging apparatus 10. It should be noted that, in an alternate embodiment, primary image 30 may be provided as raw data, requiring some amount of processing prior to storage in PACS 20. Logic processors 22 and 24 may generate secondary images 32 and 34 from raw data or from pre-processed primary image 30, as shown in FIG. 1.

Still referring to FIG. 1, an image management system 50 has a logic processor 52, a memory 54, and an operator console 56 that includes a display 58 and an operator entry device 60, such as a keyboard, mouse, touch screen, or other device for entry of operator commands. Commands at image management system 50 provide and manage the companion image associations between the original primary image 30 and its corresponding secondary images 32, 34.

Figure 2:
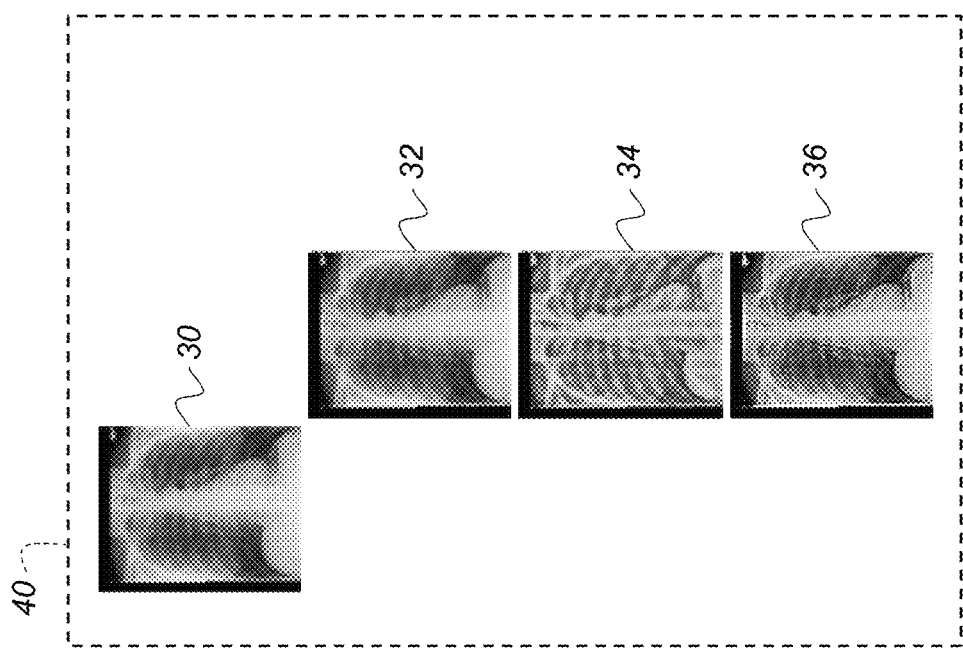
FIG. 2 is a schematic diagram that shows a set of associated companion images as defined according to an embodiment of the present invention.

The schematic diagram of FIG. 2 shows a grouping or association of companion images 40 that includes the acquired primary image 30 along with corresponding secondary images 32, 34, and 36. As emphasized earlier, each companion image in the set of companion images 40 is derived from the same original captured image data. Secondary images 32, 34, and 36 have been processed in some way to accentuate or highlight various features useful in clinical or diagnostic interpretation. The associated companion images 40 are thus of the same general type by anatomy, such as AP chest images, for example, because each associated companion image in the set of companion images is formed by processing the same acquired, primary image data.

Image management system 50 of FIG. 1 can be used to generate the grouping of companion images 40 either by explicit operator instruction or in an automated fashion, as described subsequently. The different associated images in a particular association can be stored in different places and are linked by entries that are maintained on image management system 50.

Database utilities, pointers, or other data linking elements can be used to provide the needed associations between primary and secondary companion images.

Figure 3A:
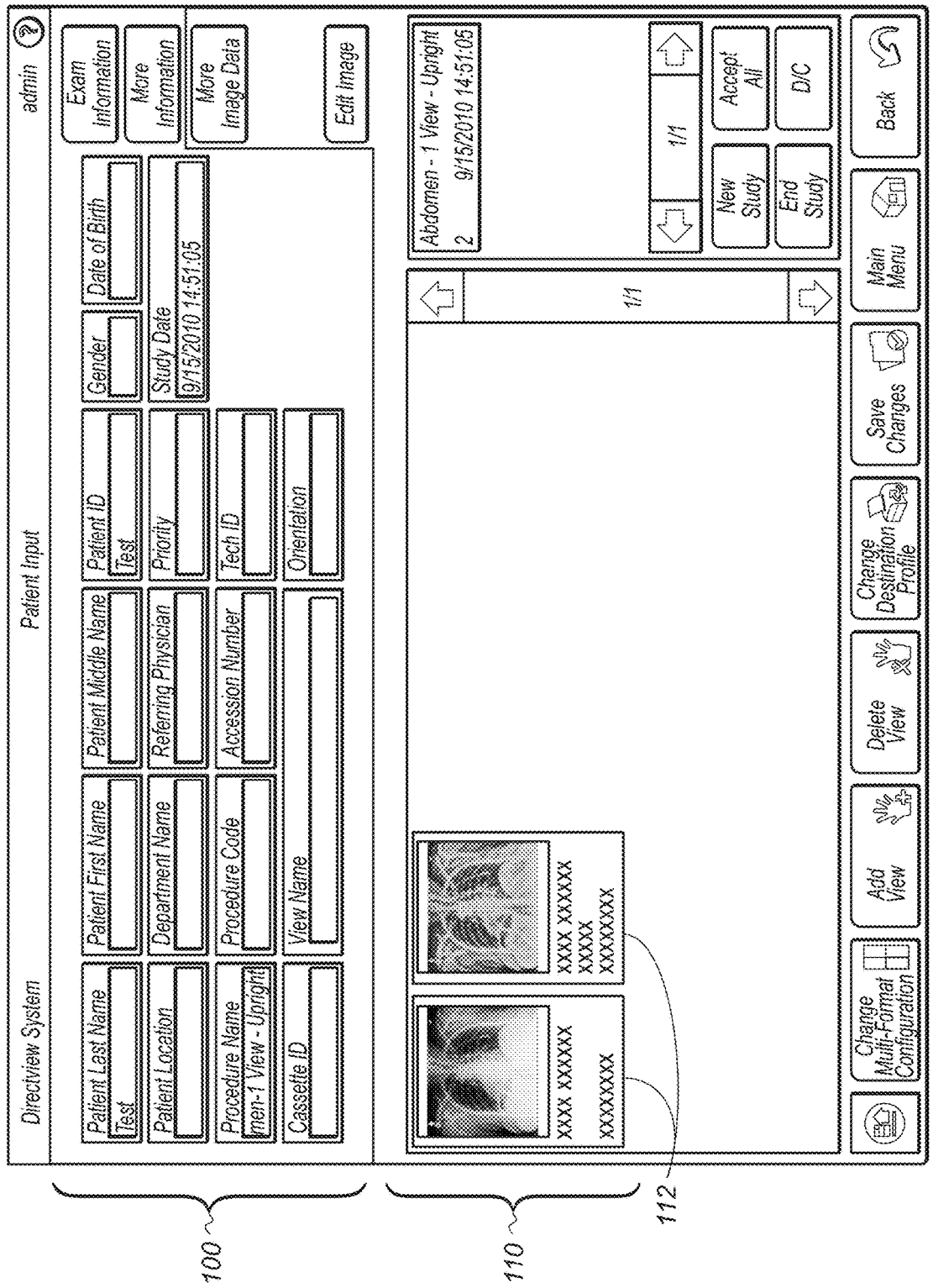
FIG. 3A is a plan view of a display screen for input of patient data and display of images stored and available for the patient.
Figure 3B:
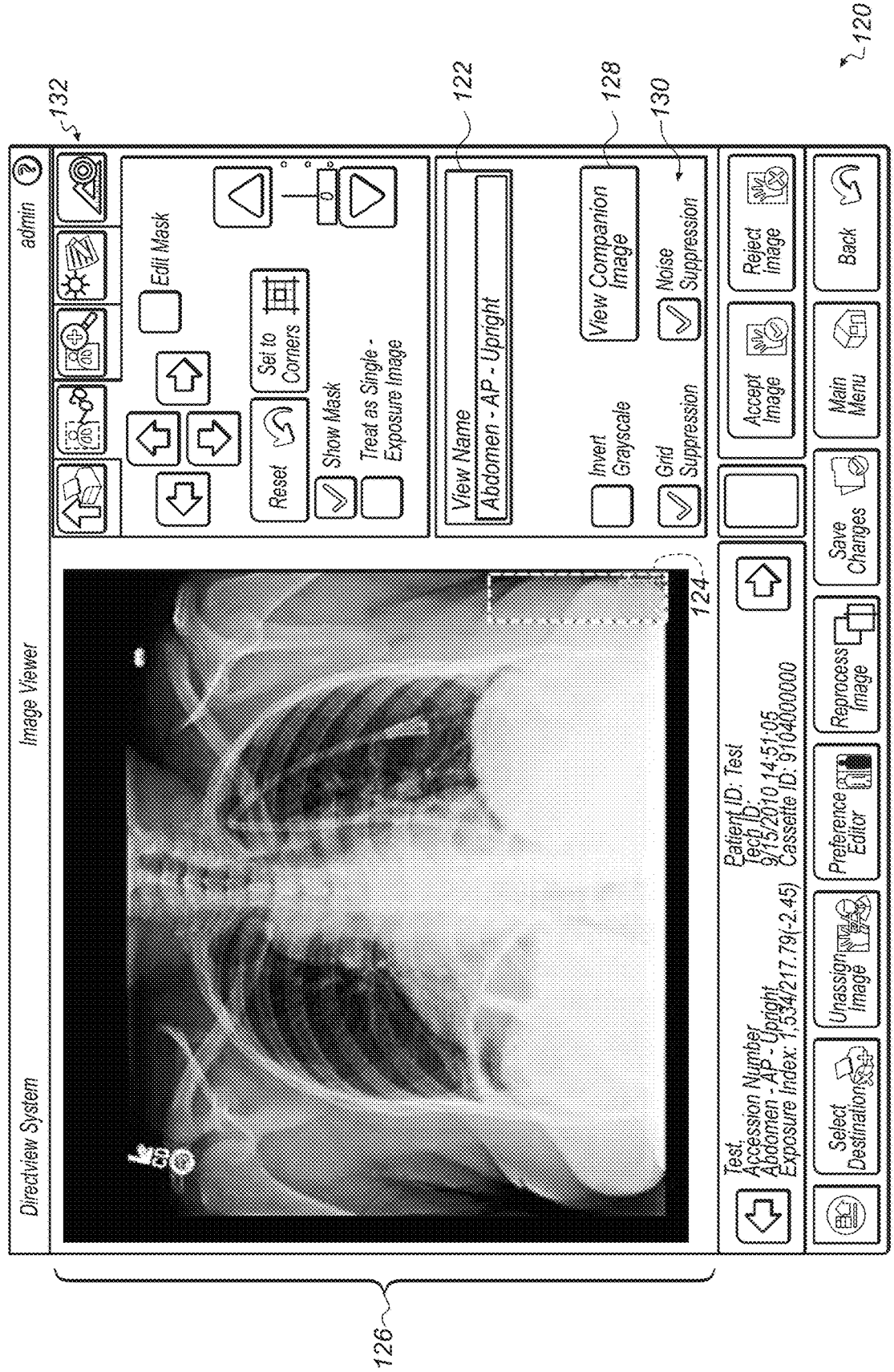
FIG. 3B is a plan view of a display screen showing an image view window with a primary image.
Figure 3C:
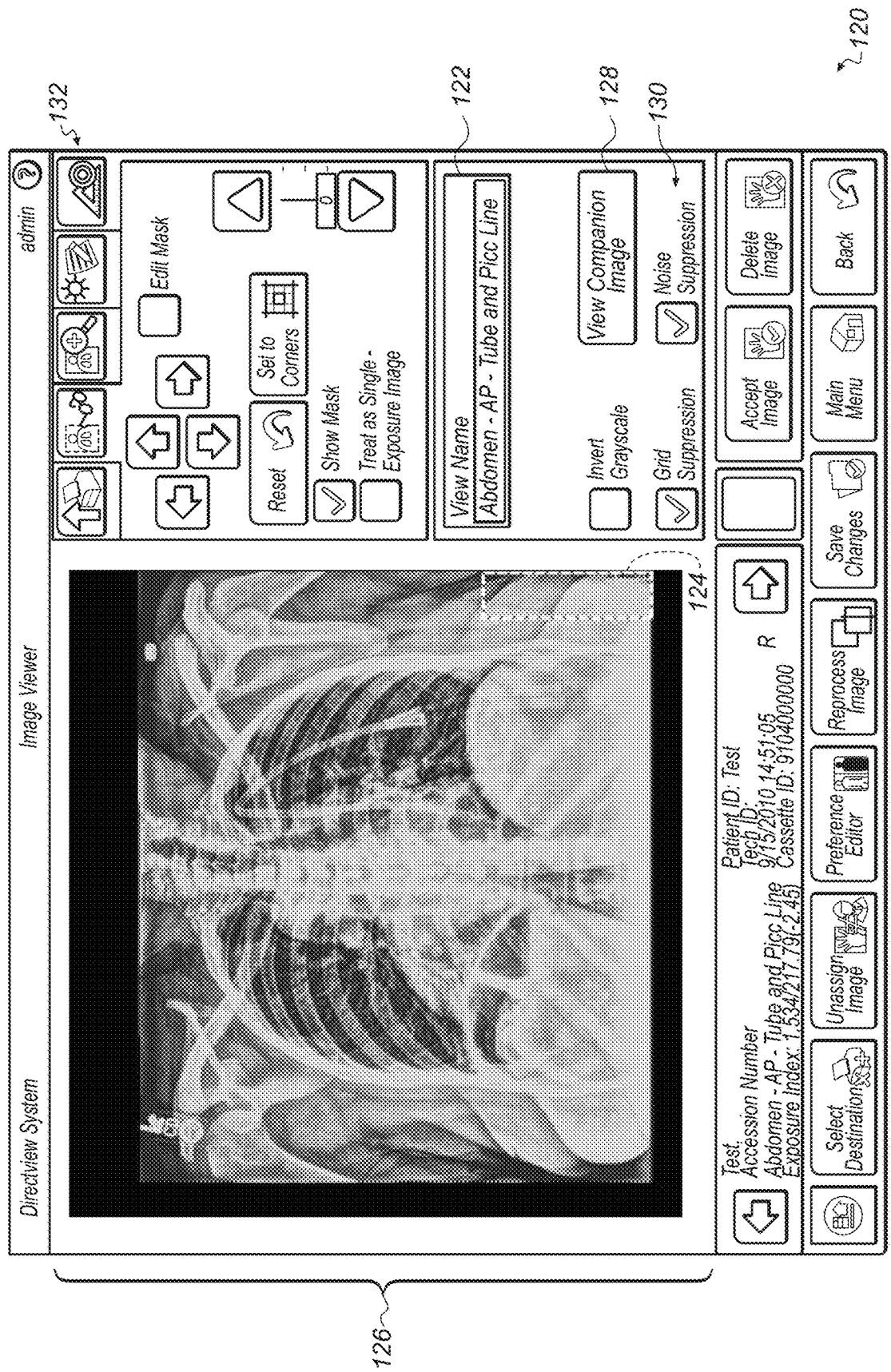
FIG. 3C is a plan view of a display screen showing an image view window with a companion secondary image.

FIGS. 3A, 3B, and 3C show plan views of a small number of operator screens provided from operator console 56 according to one embodiment of the present invention.

In FIG. 3A, a patient data window 100 displays various data from the patient record or profile, including name, identification numbers, sex, date of birth, and information on various medical procedures, as shown. A thumbnail window 110 displays one or more thumbnail images 112 that represent the primary and processed secondary images that are part of an association for the patient, as was described earlier with reference to FIG. 2. Other portions of the screen provide various functions for moving from one display to another, for adding or removing views, or for modifying the patient profile, for example.

In the embodiment shown in FIGS. 3A, 3B, and 3C, thumbnail images 112 act as executable data links to the image as it is stored at a specific computer-accessible storage location or address. By selecting a thumbnail image from the screen of FIG. 3A, the operator can view an image view window 120 as shown in FIGS. 3B or 3C. FIG. 3B shows image view window 120 with an image view area 126 for a primary image; FIG. 3C shows image view window 120 with image view area 126 for a secondary view image, such as an image having enhancement of tubing and PICC line structures, for example. A view name field 122 indicates a descriptive name assigned to the view. Other features available within image view window 120 include a text box 124 that allows entry of text or symbol annotation along an edge of or within any selected portion of an image.

FIGS. 3B and 3C also provide toggles 128 that enable rapid switching between displays of primary and one or more secondary images. A set of controls 130 provides various image processing functions such as grid suppression, noise suppression, and grayscale inversion, for example. Another set of tabs 132 provides a range of functions for display, including functions such as optional definition and editing of a black surround mask, pan, zoom, and crop functions, measurement, window level setting for pixel intensity, and markers.

Referring to FIG. 3A, thumbnail images 112 are provided to enumerate and allow access to various primary images of the patient that have been acquired and can be used to show whether or not one or more secondary images is associated, as a companion image, with the primary image.

Figures 4A, 4B:
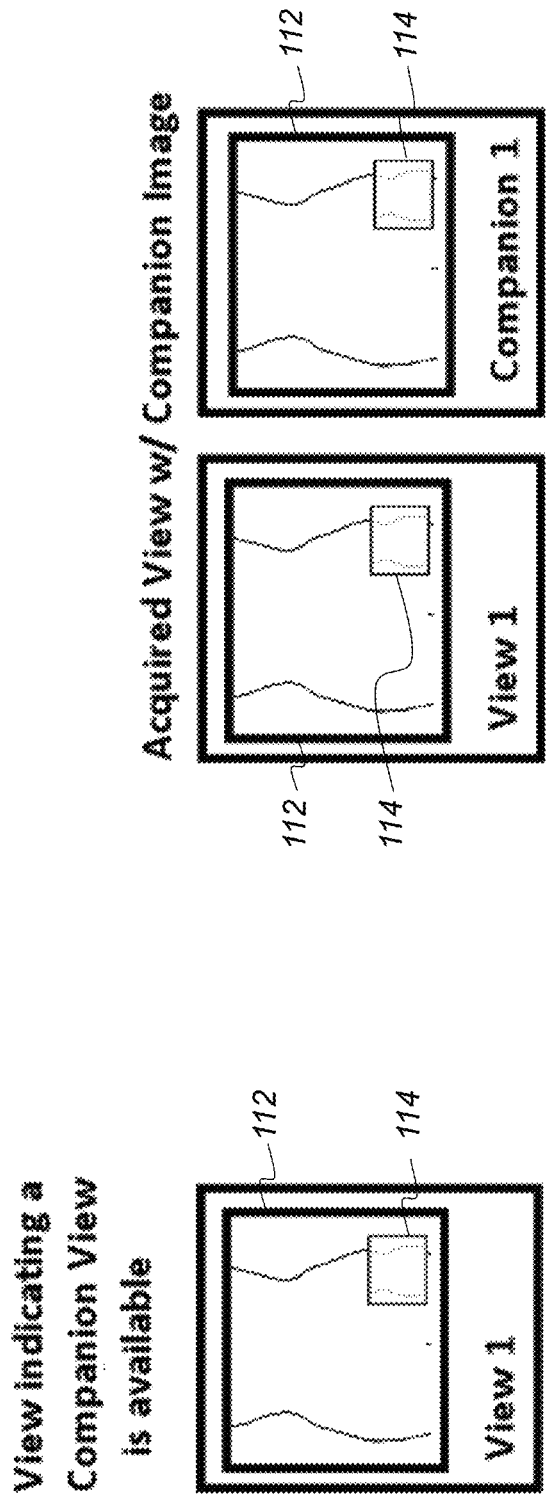
FIG. 4A is a diagram showing the arrangement of thumbnail symbols and icons for a primary image having a companion secondary image view.
FIG. 4B is a diagram showing the arrangement of thumbnail symbols and icons for primary and secondary companion views.
Figure 5:
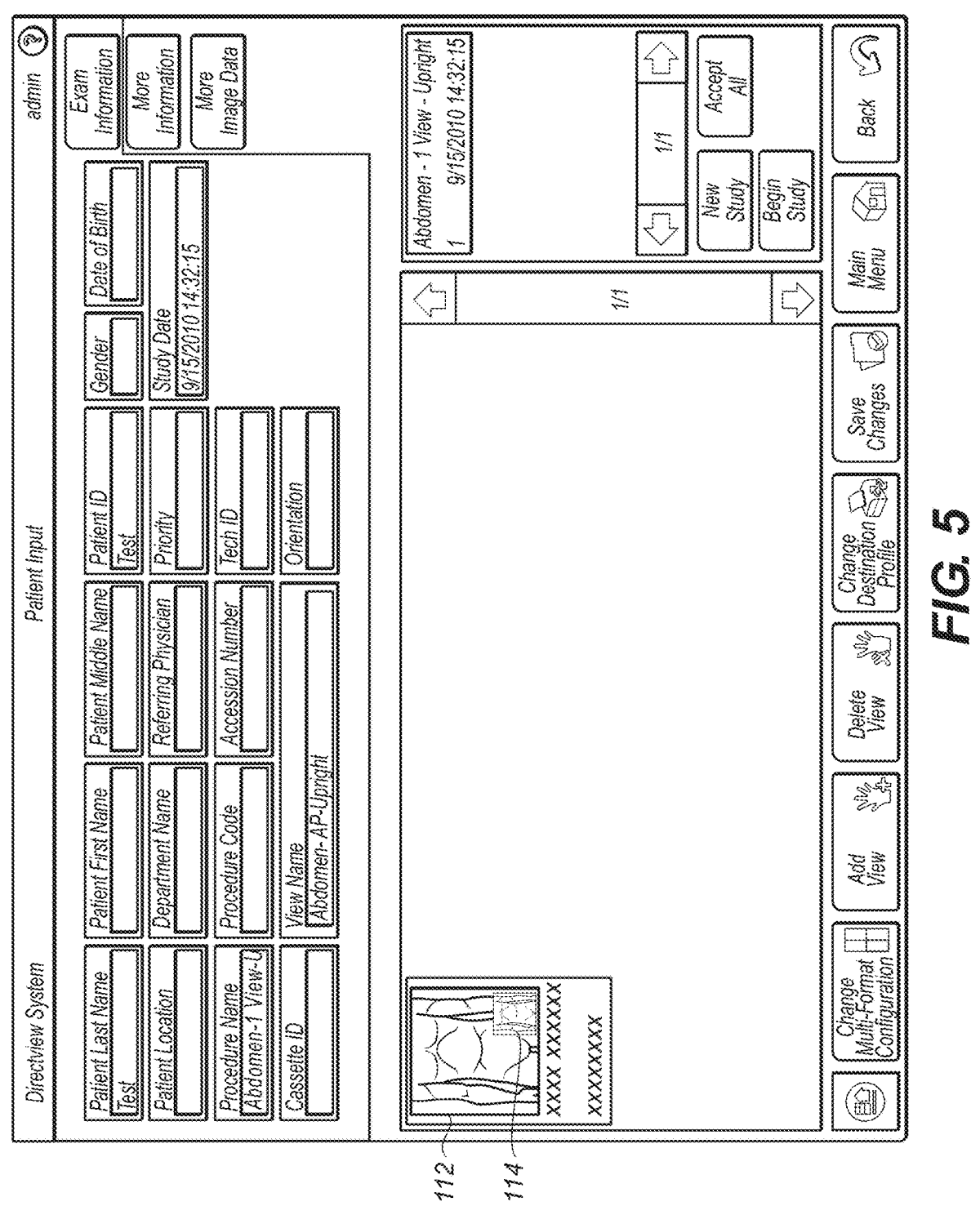

In one embodiment, as shown in FIGS. 4A and 4B, thumbnail images 112 are provided with icons 114 to indicate that images are associated as companion images. In the example shown, each icon 114 shows a miniaturized representation of the type of image that has been obtained or that can be obtained as companion image for the given image type. Administrative capability for setting up which types of images can be associated as companion images is described in more detail subsequently. The screen view of FIG. 5 shows how these symbols for primary and secondary companion images appear as part of the patient record in image management system 50 in one embodiment.

Image management system 50 also supports the workflow for accepting operator instructions to generate one or more secondary images for a given primary image. Referring to the logic flow diagram of FIG. 6, image management system 50 acquires the original or primary medical image in an acquisition step 200. A decision step 210 checks to determine whether or not stored instructions indicate automatic generation of one or more companion images. If this option has been previously set up, an automatic generation step 220 is executed to generate secondary image 32. If automatic generation has not been set up, processing proceeds to a second decision step 230. Here, the operator has the option of specifying that a secondary image be generated. In an initiated generation step 240, the operator enters a command that generates an instruction to generate one or more secondary images 32. Otherwise, generation of secondary images is skipped.

Figure 6:
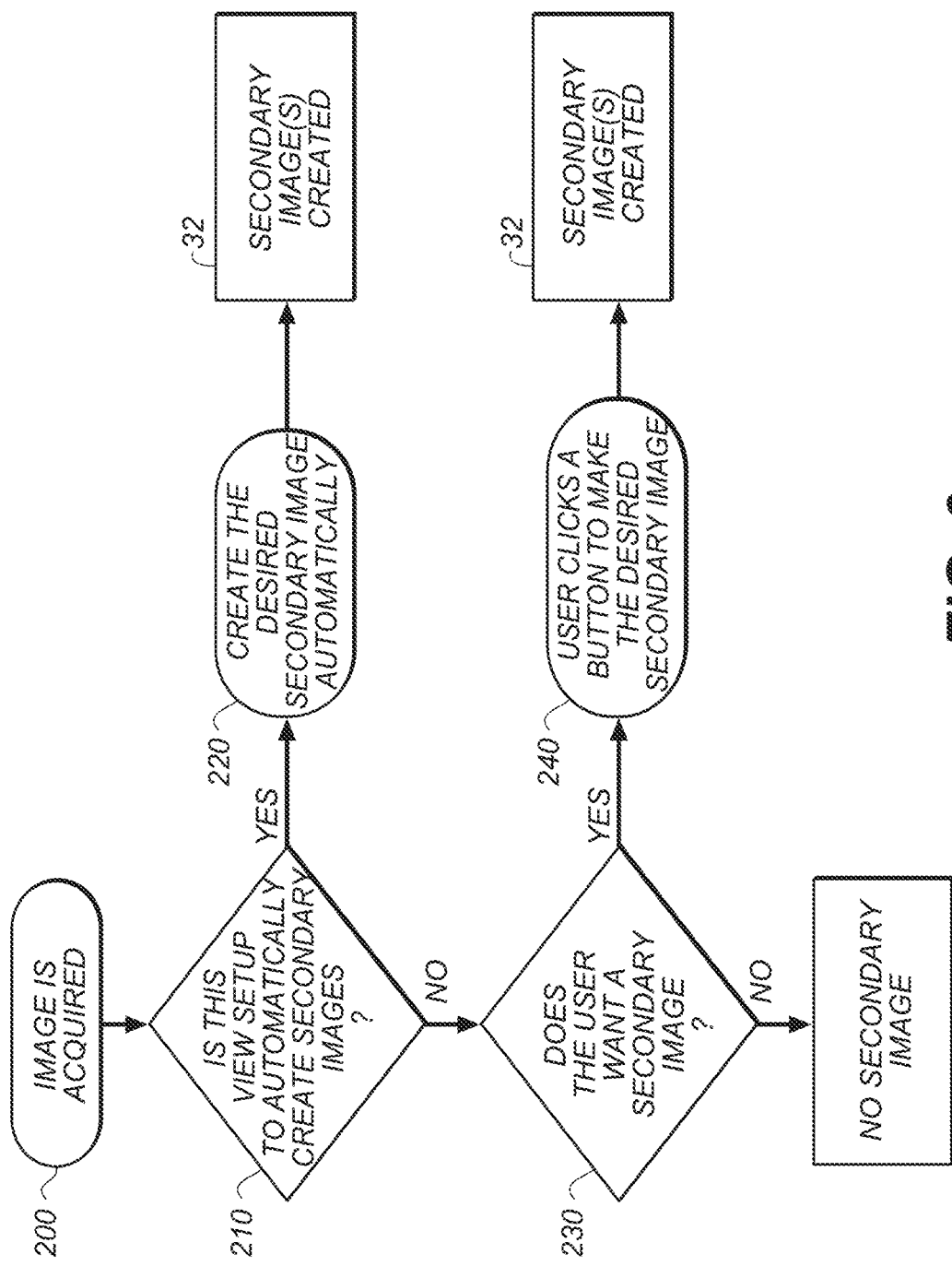
FIG. 6 is a logic flow diagram showing the basic sequence that is executed to generate secondary images following primary image acquisition.

As the sequence of FIG. 6 shows, an automatic generation capability is provided for generating one or more secondary views when a primary image is acquired.

Figure 7:
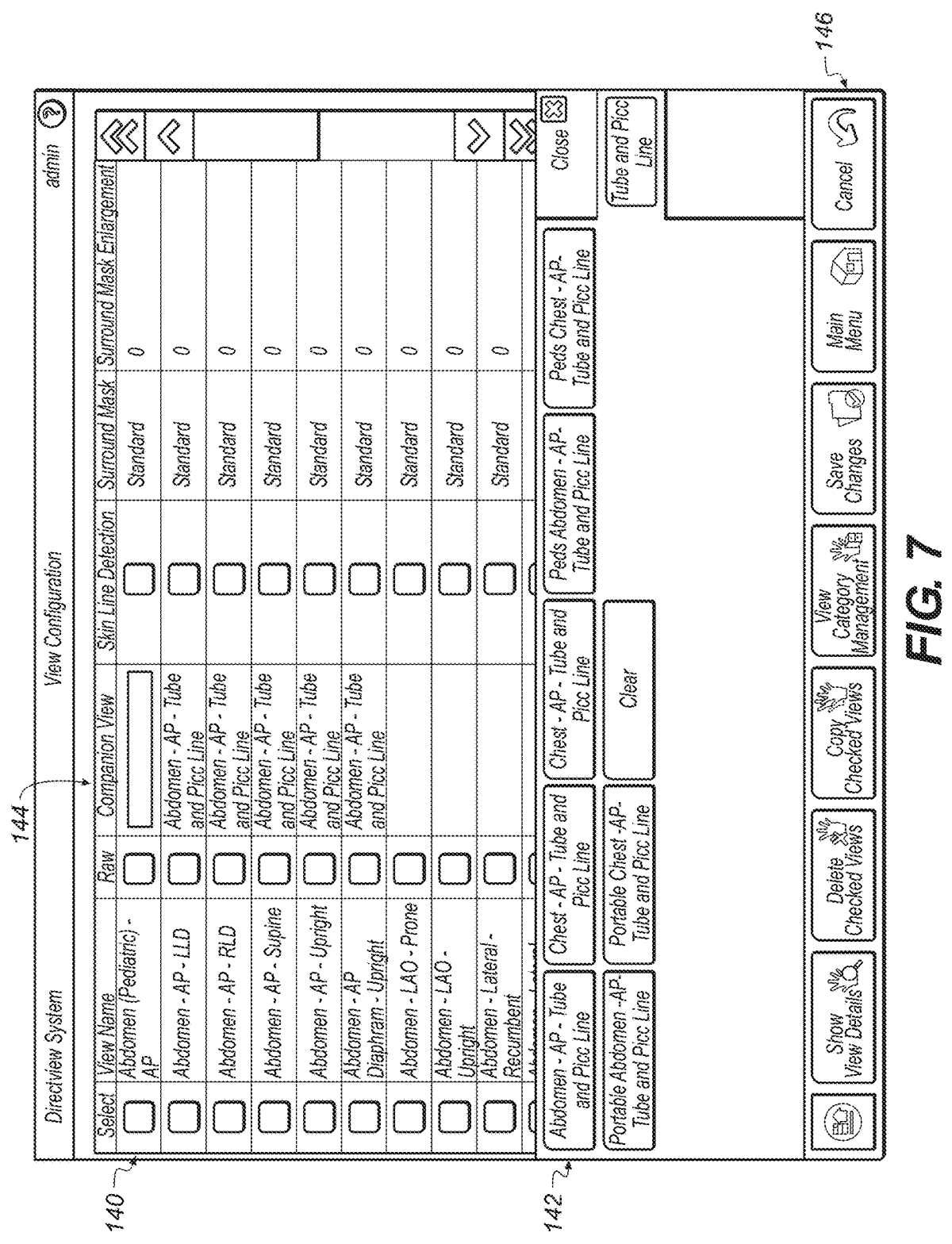

The operator interface screen of FIG. 7 shows a utility for setup of the needed primary- secondary image associations according to one embodiment of the present invention. This setup can be performed for all patients at a site or for any individual patient, as needed. The setup is used to designate what type or types of secondary image can be generated for each type of image that can be acquired. Each standard type of x-ray image lists in the View Name column, a view list 140. The operator first selects a particular view type. In response, the system displays controls in a companion selection keypad 142 as a management utility to specify one or more available secondary views that can be associated as a companion view with the selected view type. In one embodiment, for example, operator selection of a chest AP view in view list 140 automatically displays controls in companion selection keypad 142 for chest AP tube and PICC line, pneumothorax-enhanced, contrast-enhanced, and rib suppressed images. The one or more selected companion secondary views then list in a companion view column 144. Other optional selections can be made for image presentation treatment, such as selection of a pre-defined surround mask or other option. Another set of controls 146 then enable the operator to save or modify the specified associations.

It is noted that not all image types may have a corresponding secondary view. With some types of images, only a primary image is obtained.

Figure 8:
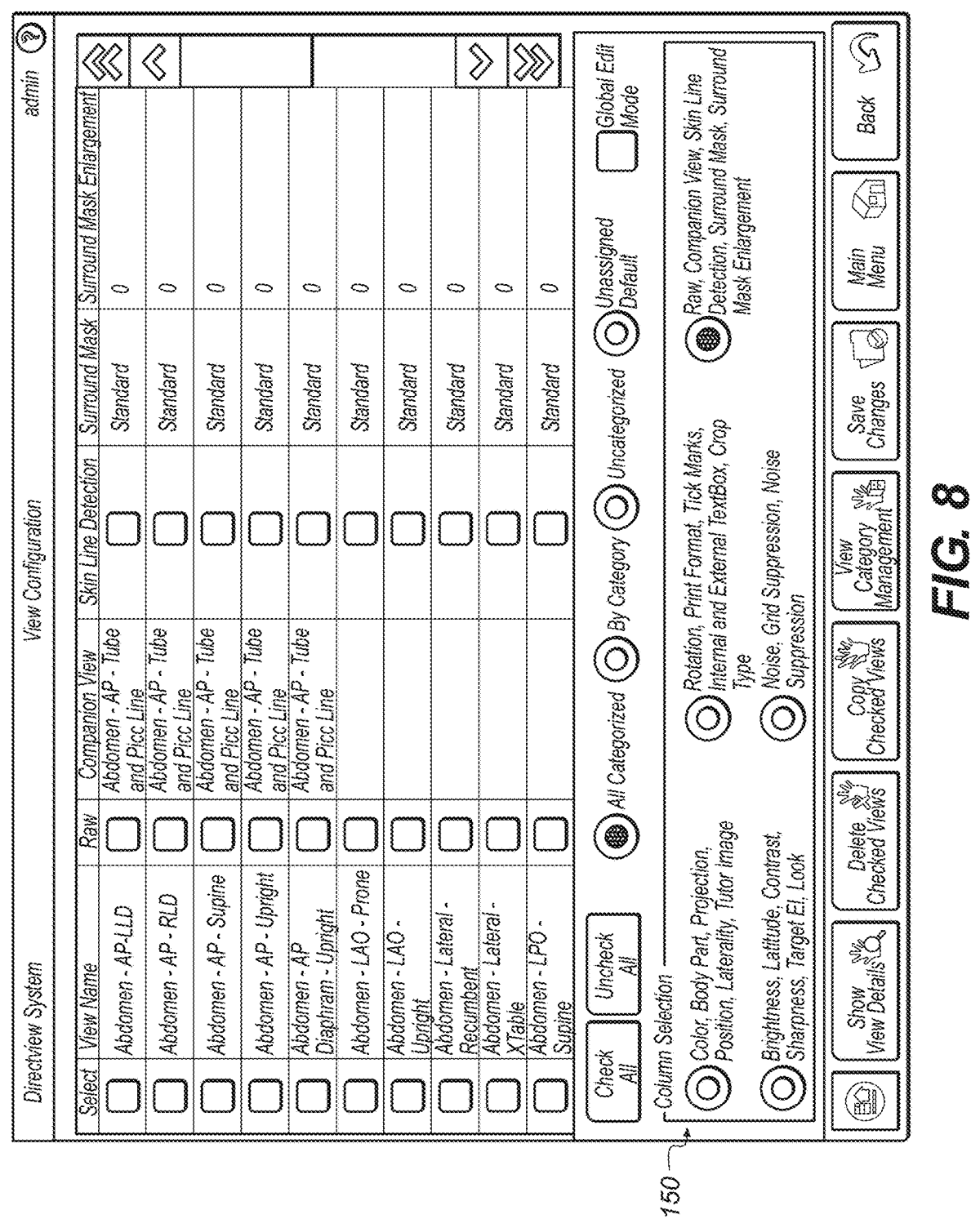

A number of configuration utilities are available for the system operator or administrator of image management system 50 of the present invention. The configuration screen of FIG. 8 is used to set up the operator interface screen of FIG. 7, assigning column types and arranging what type of information will be presented on the screen. A set of controls 150 designate column fields for organizing the image content that is available for a patient.

Figure 9:
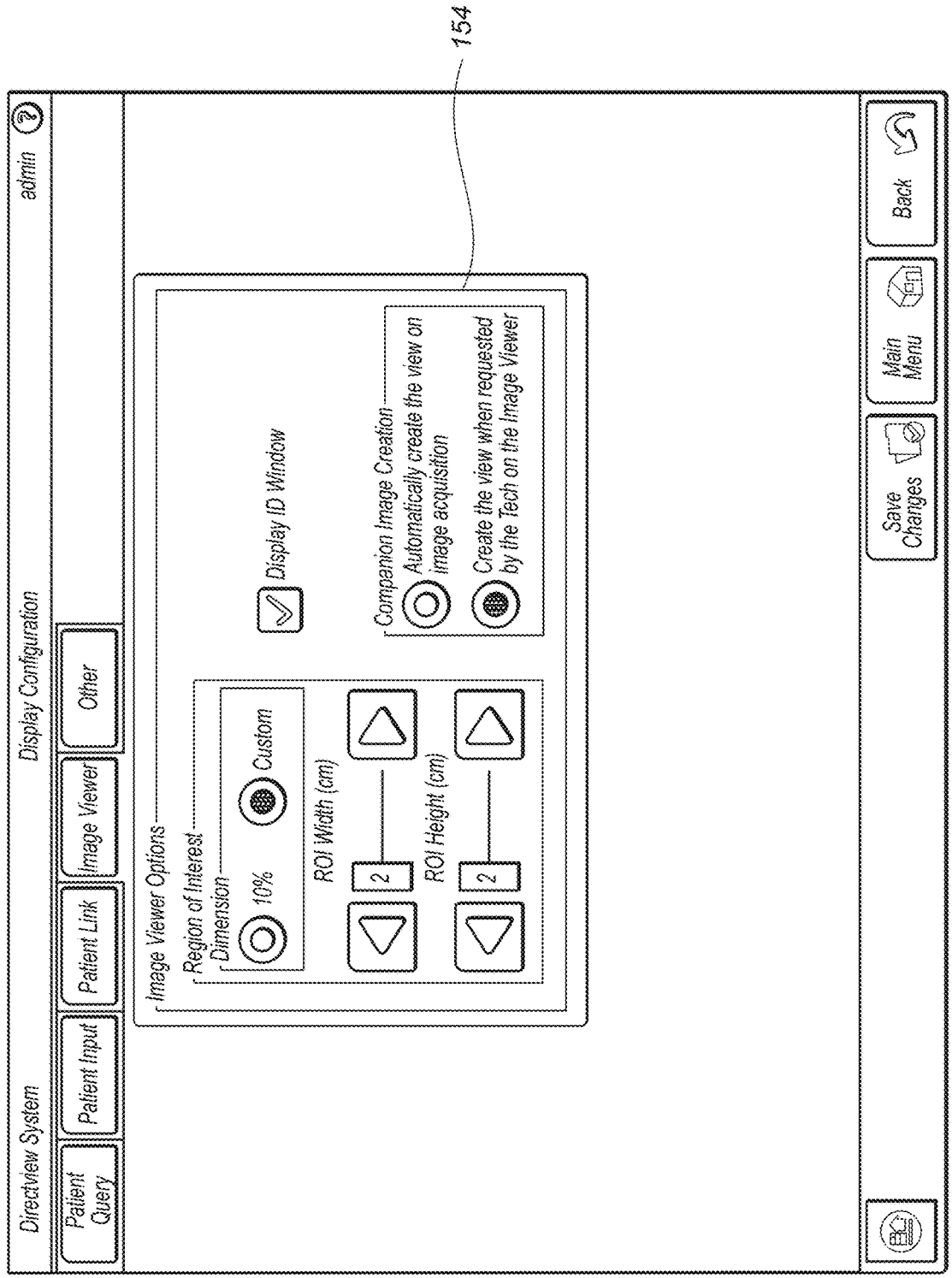
FIG. 9 is a plan view of a display screen used for determining whether or not a secondary image is obtained automatically upon acquisition of a primary image.

As noted with reference to the logic flow diagram of FIG. 6, the secondary image can be automatically generated or secondary image generation can be independently initiated upon entry of an instruction by the operator. The operator interface screen of FIG. 9 shows controls 154 for setup of automatic initiation. Additional controls are provided for other image viewer options, such as size of the region of interest (ROI), for example.

Figure 10:
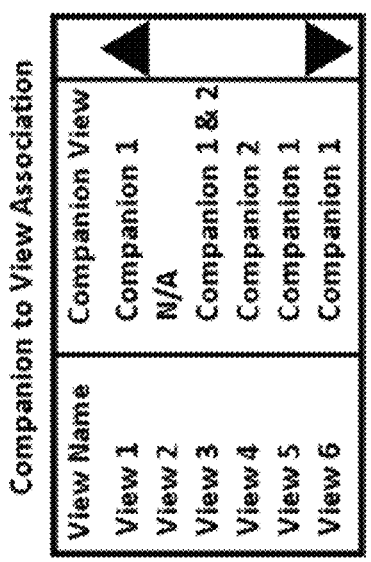
FIG. 10 is a diagram showing the association of primary and secondary images.

FIG. 10 shows an alternate type of association interface that can be used to list and arrange the correlation between the various types of primary images as views and their corresponding associated secondary views.

A number of other administrative utilities and capabilities are also provided in embodiments of the present invention. For example, the secondary image can be deleted if desired, while retaining the original primary image. However, if the primary image is rejected from the system, its associated secondary companion images are also deleted. The system also provides the ability to delete the secondary image without deleting the original primary image.

In addition, the system can automatically print or deliver the multiple renderings for a single exposure with one user action, for example, a selection of an icon or press of a button. Side-by-side printing, with the primary image on the same sheet as one or more secondary images, is provided in one embodiment. All renderings of the same original image can be selected or deleted with a single user action.

Figure 11:
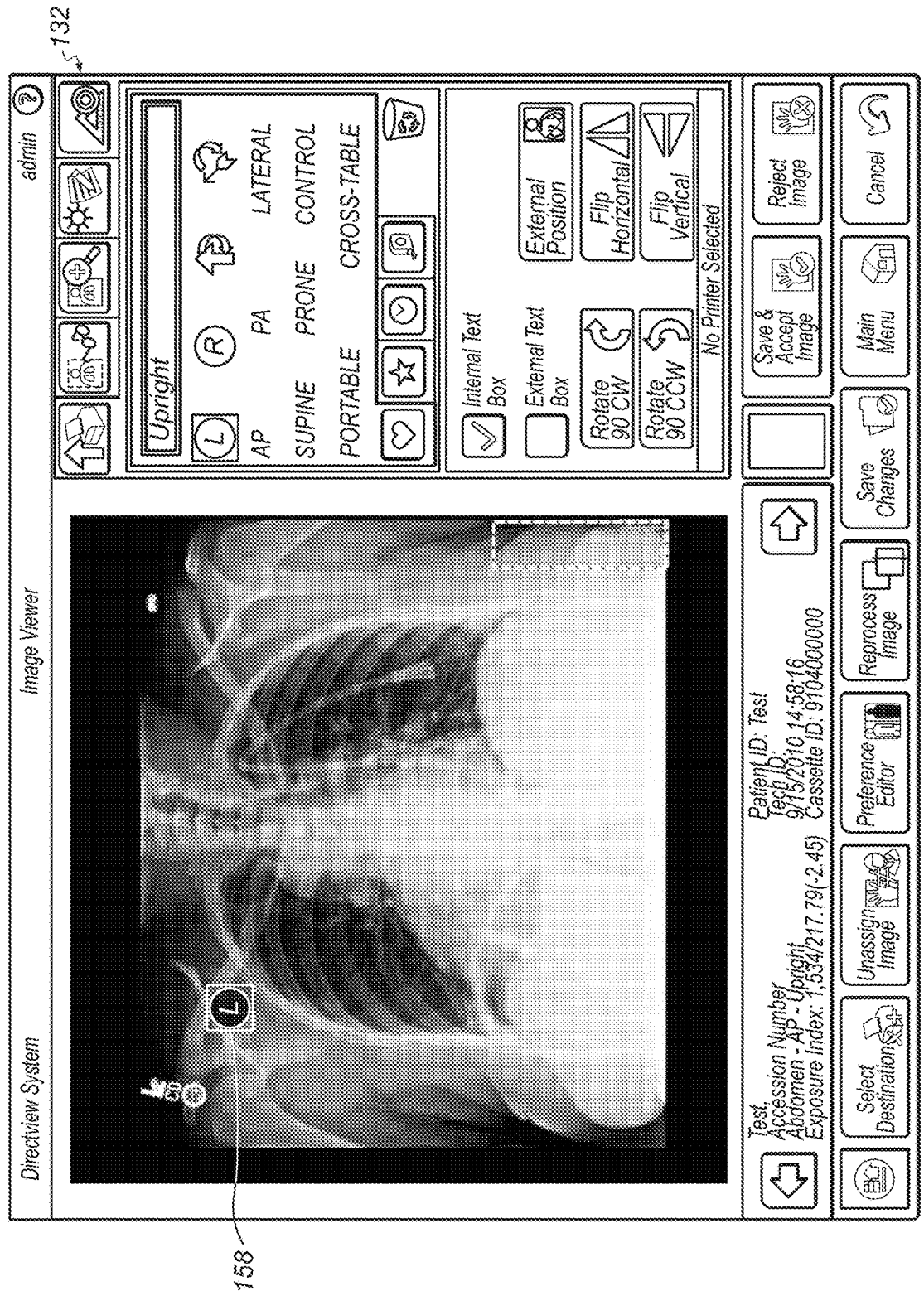
FIG. 11 is a plan view of a display screen showing utilities for marker and text box placement.

It is often desirable to enter annotation or to provide cropping or other treatment to an image to improve usability or to record observations. Embodiments of the present invention allow the operator to apply these changes to each companion image in the set of images obtained for a patient or other subject. Using this capability, edits made to one image can be applied to all of its companion images. As noted earlier with reference to FIGS. 3B and 3C, tabs 132 include various sets of controls for performing various operations on the image data. Referring to FIG. 11, a tab 132 provides operator access to various markers and print settings. Using the utilities on this tab, the viewer is able to place markers 158 of various types onto any of the associated companion images. When this placement is saved, the marker 158 then appears on the other associated companion images for the same patient. Thus, for example, placing a marker on a companion secondary image effectively includes the same marker in position on other secondary images that are companion images of the same image and on the primary image as well. Similarly, placement on the primary image affects each of its associated companion secondary images. Various arrangements of text and symbols can be provided for annotation. Text box placement internal to the image area or outside the image area is selectable, along with features such as text position, content, and direction (vertical or horizontal). This capability can be selectively disabled in one embodiment.

Figure 12:
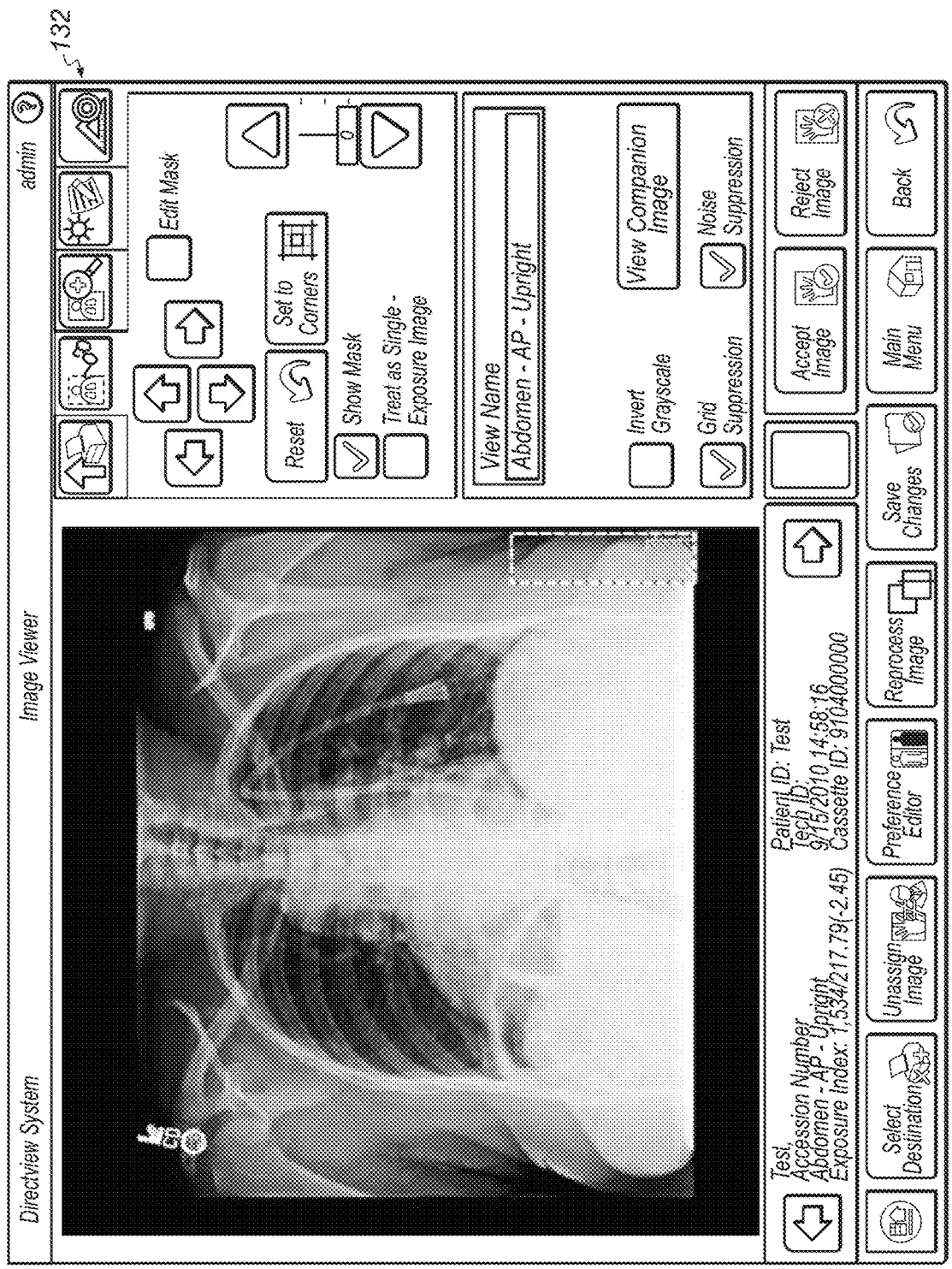
FIG. 12 is a plan view of a display screen showing utilities for entry of a mask and other view options.
Figure 13:
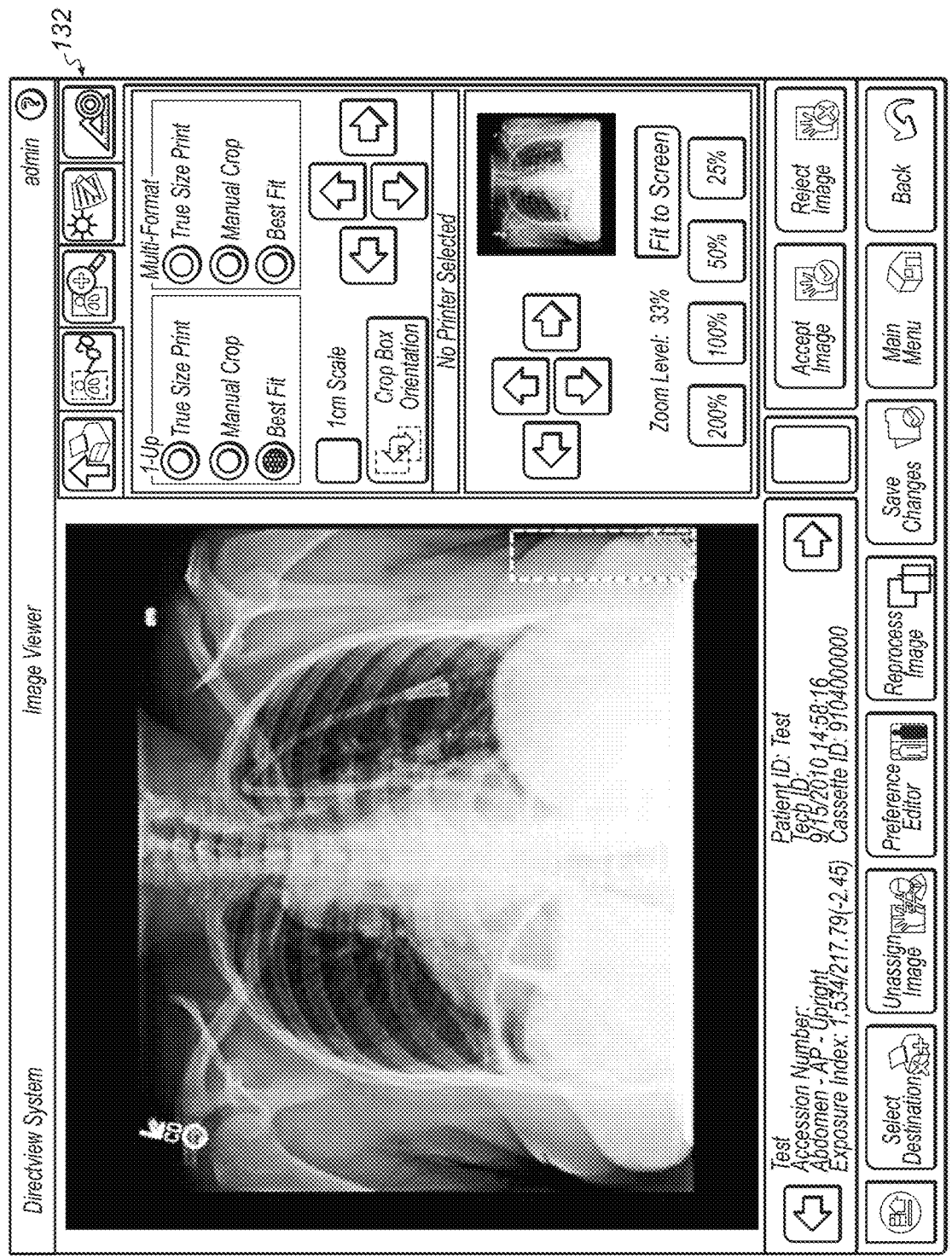
FIG. 13 is a plan view of a display screen showing utilities for different print options and pan/zoom operation.

The tab 132 selection shown in the example of FIG. 12 allows the operator to define and edit a black surround mask and to enter various view options. The tab 132 selection given in the example of FIG. 13 gives the operator access to a number of different print or display presentation options and pan/zoom operation as well as to utilities that enable local magnification or localized image enhancement centered over a specified area of an image rather than over the whole image. Print and display presentation options include print sizing and cropping.

Figure 14:
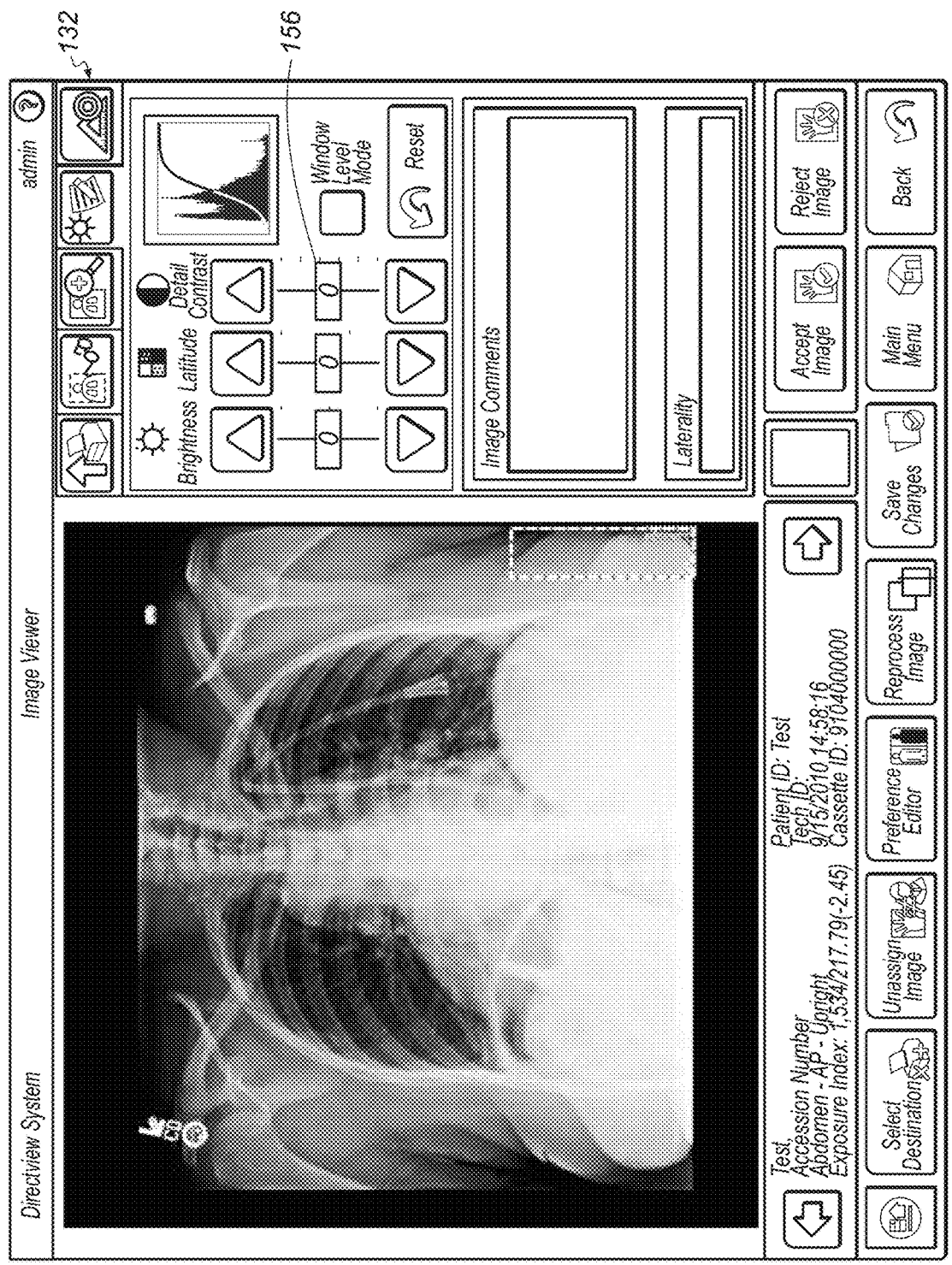
FIG. 14 is a plan view of a display screen showing various controls used for display window settings.
Figure 15:
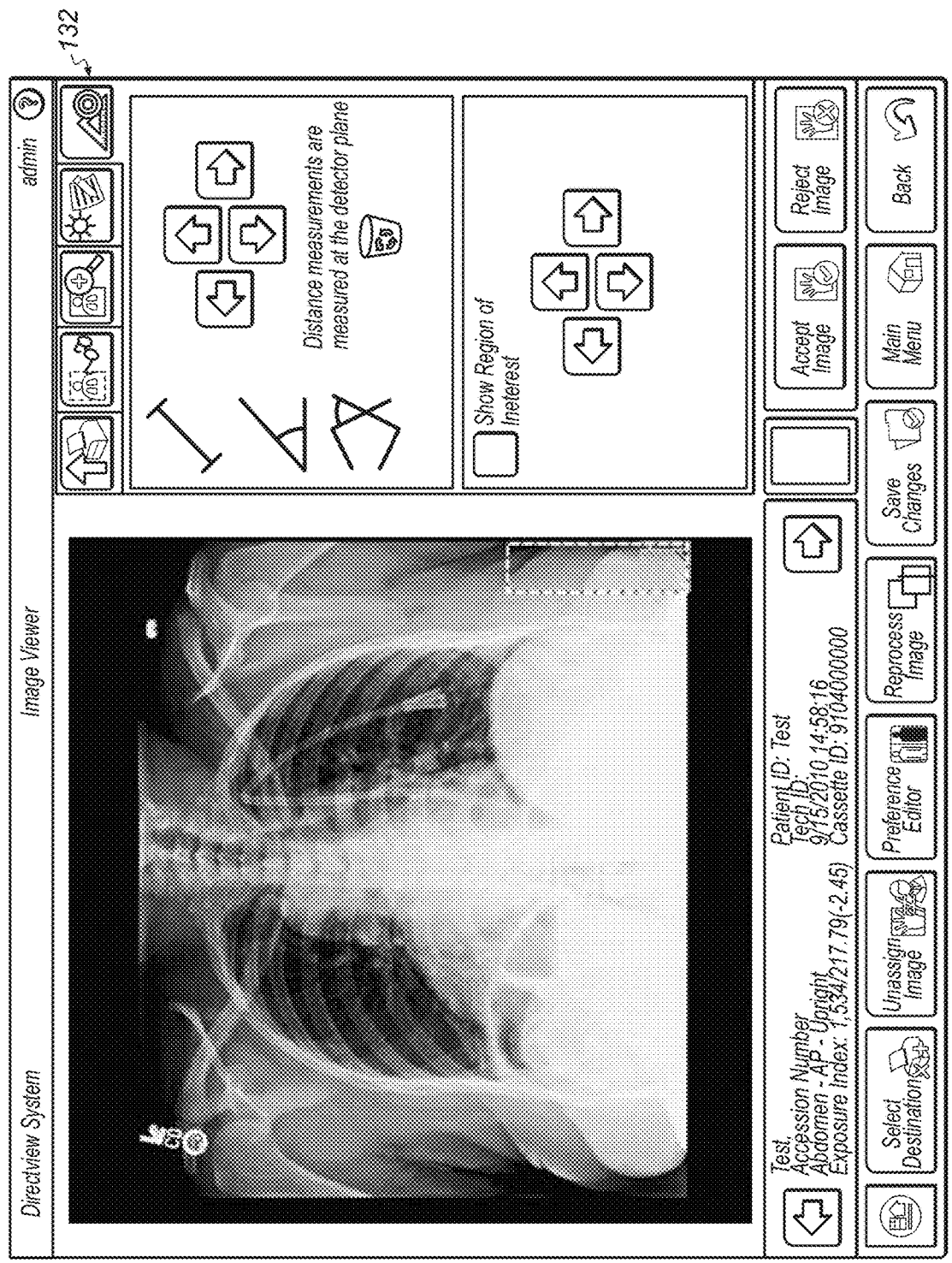
FIG. 15 is a plan view of a display screen that provides a linear and angular measurement utility.

The tab 132 selection given in the example of FIG. 14 includes various controls used for display window settings. In the embodiment shown, dials 156 are used to set on-screen characteristics such as brightness, contrast, and latitude, for example. The tab 132 selection given in the example of FIG. 15 shows a measurement utility for providing distance or angular measurements. Measurement data can be retained as annotation in a number of ways or may be discarded. By default, measurement data appears on all associated companion images, that is, on the primary image and on any of its secondary images.

Figure 16:
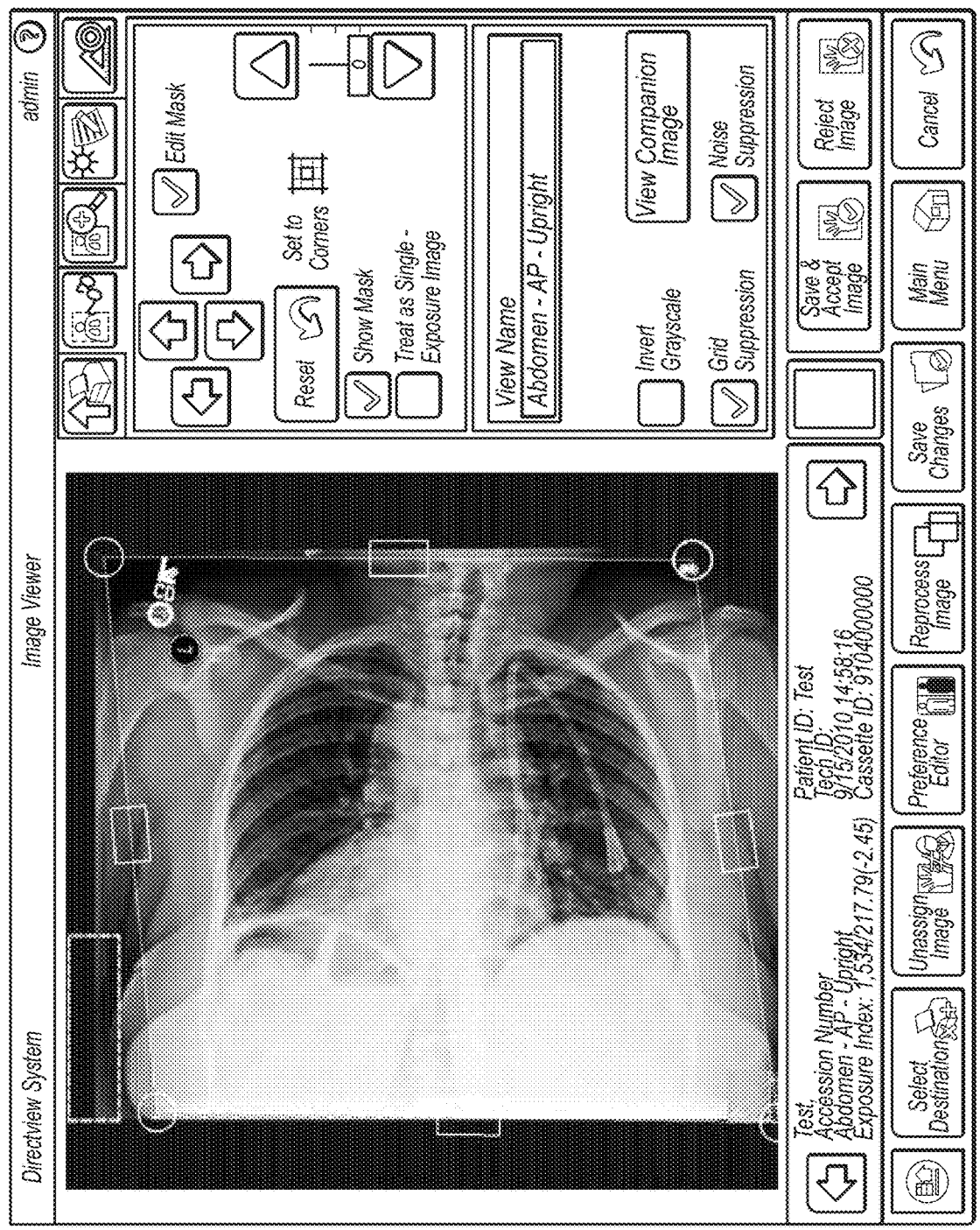
FIG. 16 is a plan view of a display screen showing rotation and definition of a non-rectangular mask.
Figure 17:
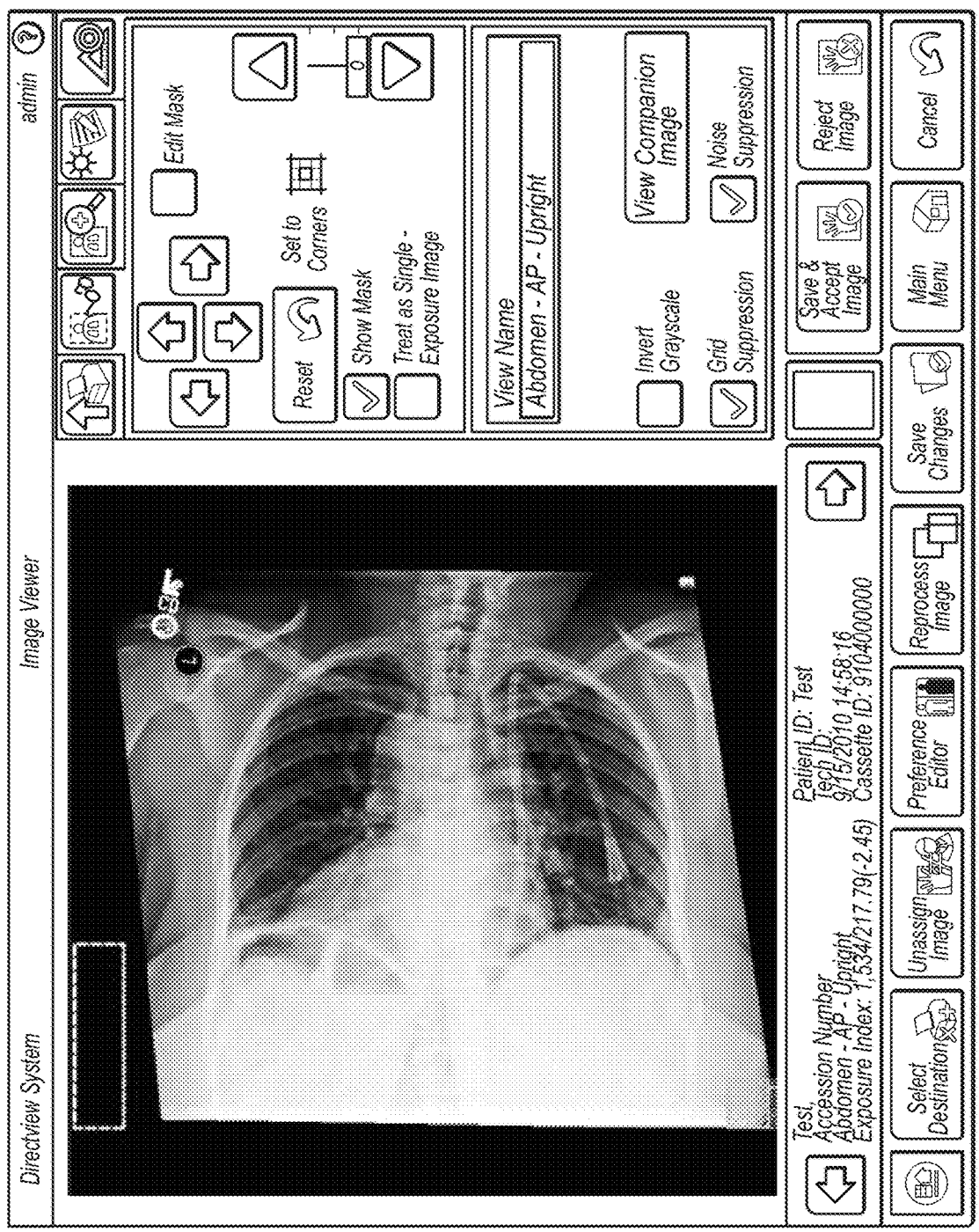
FIG. 17 is a plan view of a display screen with the mask of FIG. 16 enabled.
Figure 18:
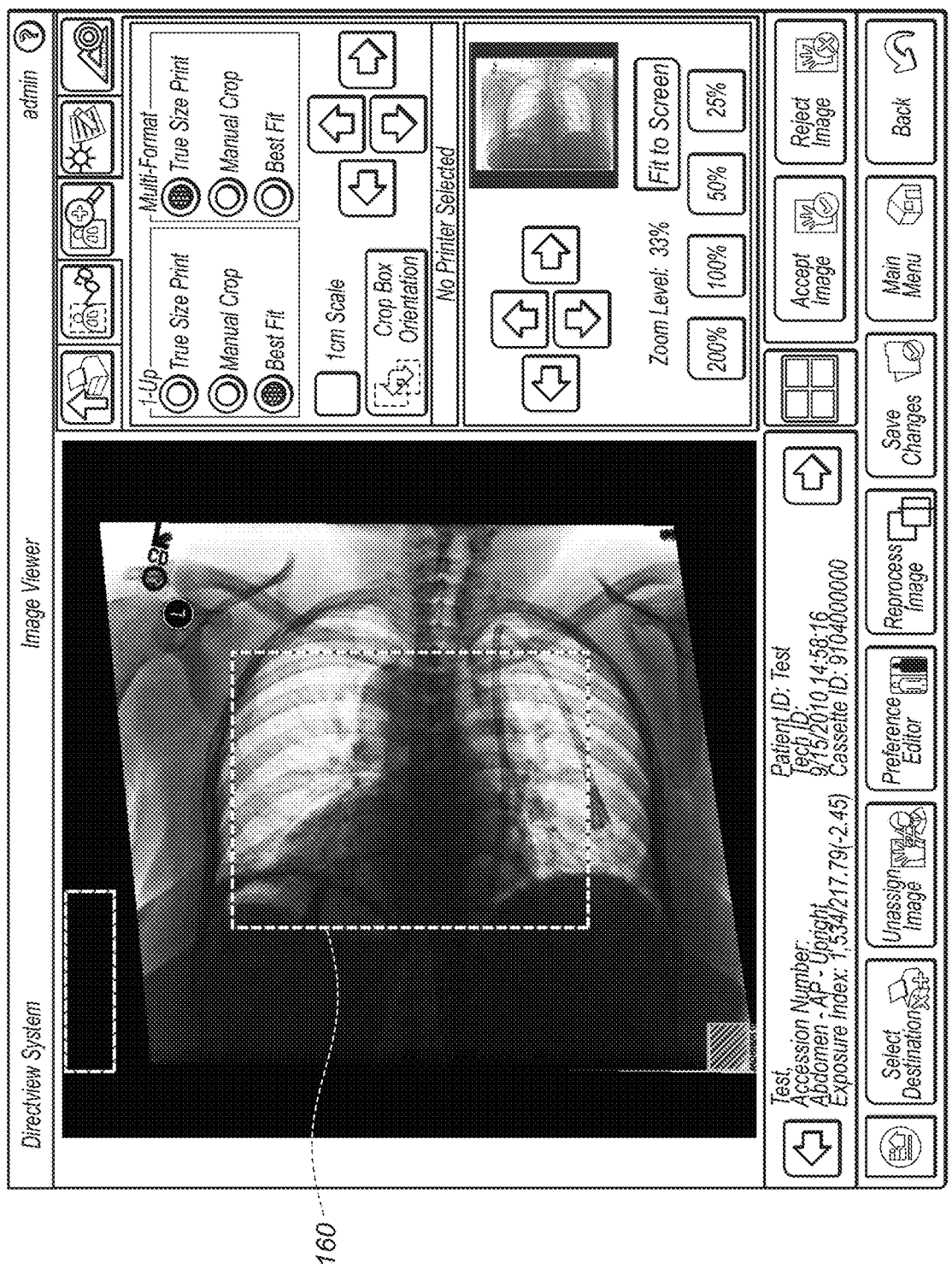
FIG. 18 is a plan view of a display screen with the mask of FIG. 16 with gray scale inversion.

FIGS. 16 and 17 show an example sequence in which the image has been rotated, then cropped. Noise suppression and grid suppression are also provided. The example of FIG. 18 shows the inversion of grayscale that can be used to help discern various features in the image. A region of interest 160 is outlined on the image. As is true for other types of image modification and annotation, outlining of region of interest 160 is also executed on each of the companion secondary images and on the primary image in the set of companion images.

Figure 19:
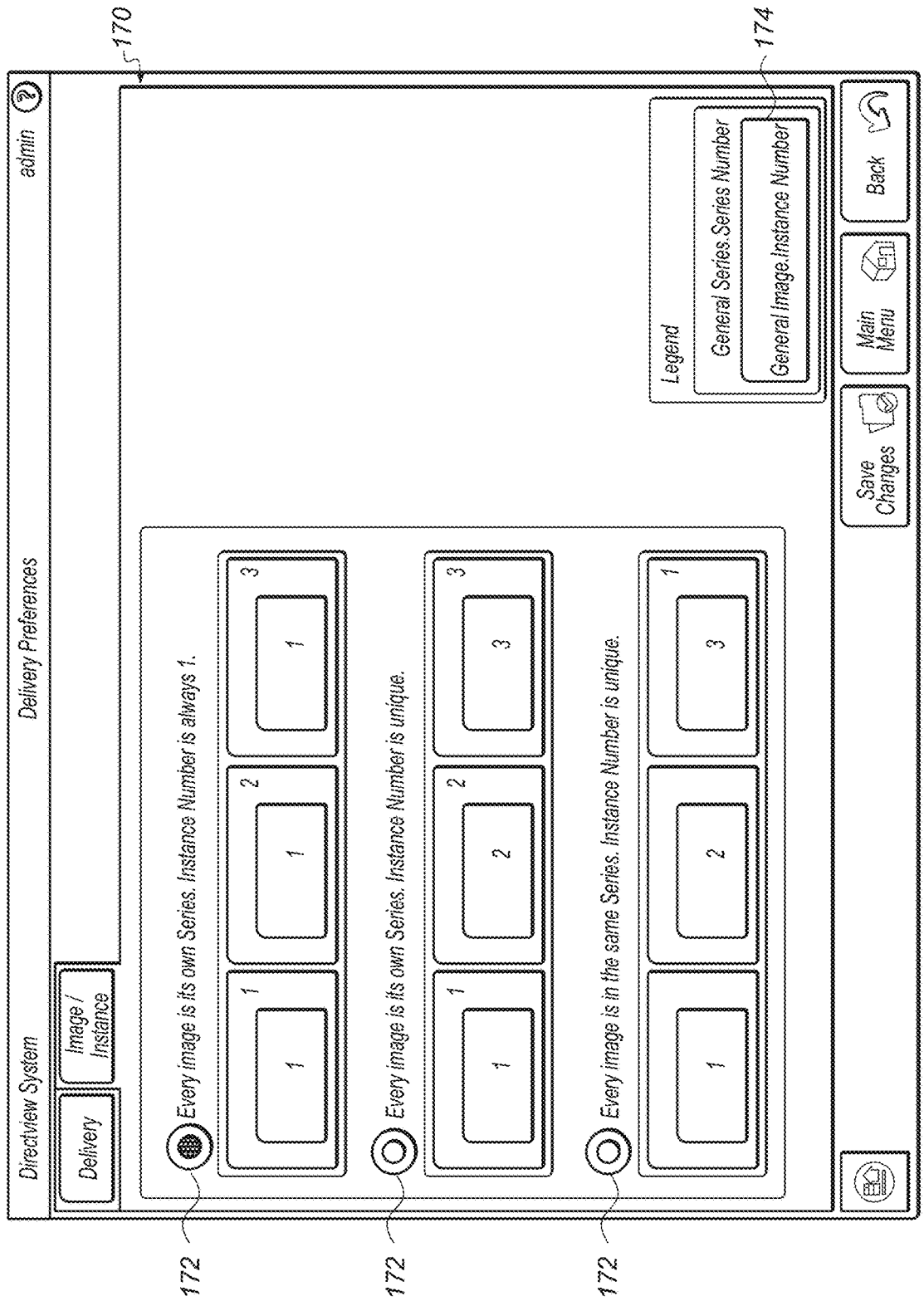
FIG. 19 is a plan view of a display screen showing operator assignments for DICOM series delivery format.

Images obtained and managed by image management system 50 of the present invention can be stored, accessed, and transmitted to other systems according to the Digital Imaging and Communications in Medicine (DICOM) standard. Using the DICOM arrangement for image data, every delivered image is part of a Series. Each companion image, as the term is defined herein, can be part of the same series or can be in a unique series. In DICOM delivered images, the series can have a defined presentation state that applies the same editing treatments to all images that are in the series. Where the unique series option applies, the Instance Number within the series can be 1 or can be unique. An exemplary Delivery Preferences window 170 shown in FIG. 19 provides controls 172 that enable the operator to choose the DICOM delivery format for a set of companion images. In another option (not shown in the example of FIG. 19), secondary companion images are delivered as alternate presentations of the same image. A legend control 174 enables assignment of a general image instance number to a series.

It can be recognized by those skilled in the graphical user interface arts that windows and display screens presented herein are representative of ways to perform various functions and could be presented in any number of alternate ways, with command entry and data field information provided using any of a number of suitable methods. For example, entry of an instruction could be initiated using any of a number of types of on-screen command buttons, selected using a computer mouse, touch screen, or other utility, or by interpreting an audible command. An executable data link that relates to the storage address or location of a companion image can be presented as one or more of a thumbnail image, a text field, a command button, and an on-screen icon, as shown variously in FIGS. 5 and 11-18 for example.

As noted earlier, the apparatus and methods of the present invention, while described primarily with reference to radiographic images of a patient can also be applied to radiographic imaging of other subjects, including NDT imaging in which radiographic images may be provided with different processing treatments in order to accentuate different features of the imaged subject.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for presenting a projection radiographic image of a subject, the method executed at least in part on a computer system, the method comprising:
    processing only one projection radiographic image of the subject to generate a first companion image and a second companion image, wherein the first and second companion images are of a same view of the subject as the projection radiographic image of the subject, and wherein the first and second companion images are each globally processed differently to provide a different global presentation for each of the first and second companion images on a computer display;
    electronically linking the first and second companion images in the computer system;
    displaying the first companion image of the subject and an operator selectable icon on the computer display, the displayed operator selectable icon disposed on or near the displayed first companion image of the subject to indicate that the second companion image is electronically accessible to be displayed on the computer display; and
    in response to an operator selection of the icon, displaying the second companion image on the computer display.

2. The method of claim 1, further comprising:
    executing an operator command to modify the displayed second companion image; and
    applying the operator modification to the first and second companion images for a subsequent display of any one of the first and second companion images.

3. The method of claim 1, wherein the step of displaying the operator selectable icon comprises displaying a representation of the second companion image on or near the displayed first companion image.

4. The method of claim 1, wherein the step of displaying an icon comprises displaying a text or symbol on or near the displayed first companion image of the subject.

5. A computer program product embodied in a non-transitory computer-readable storage medium for processing a projection radiographic image of a subject, the program having instructions that, when executed on a computer, causes the computer to perform the steps of claim 1.

6. A method for presenting a projection radiographic image of a subject, the method executed at least in part on a computer system, the method comprising:
   processing only one projection radiographic image of the subject to generate a first companion image and a second companion image, wherein the first and second companion images are of a same view of the subject as the projection radiographic image of the subject, and wherein the first and second companion images are each globally processed differently to provide a different global presentation for each of the first and second companion images on a computer display;
   electronically linking the first and second companion images in the computer system;
   displaying an annotation on the computer display to indicate that the first and second companion images are linked such that the first and second companion images are electronically accessible to be displayed on the computer display;
   displaying either or both of the first and second companion images in response to an operator input selecting the annotation;
   executing an operator command to modify either one of the displayed first or second companion images; and
   applying the operator modification to the first and second companion images for a subsequent display of any one of the first and second companion images.

7. The method of claim 6, wherein the first companion image is generated by processing raw image data originating from a radiographic imaging system and wherein the second companion image is generated by processing the first companion image.

8. The method of claim 6, wherein the first companion image comprises raw image data originating from a radiographic imaging system and wherein the second companion image is generated by processing the same raw image data originating from the radiographic imaging system.

9. The method of claim 6, wherein the step of applying the operator modification comprises one or more of applying a digital marker, grid suppression, image rotation, masking, local magnification, cropping, linear measurement, annotation, and angular measurement.

10. The method of claim 6, wherein the step of applying the operator modification comprises one of adding, editing, positioning, and removing text or a symbol.

11. The method of claim 6, wherein the step of displaying an annotation comprises displaying one or more of a thumbnail image, a text field, a command button, and an on-screen icon.

12. A method for presenting a projection radiographic image of a subject, the method executed on a computer system, the method comprising:
   displaying, on a display, a first projection radiographic chest image of the subject, wherein content of the first projection radiographic chest image comprises a Peripherally Inserted Central Catheter (PICC);
   in response to receiving a predetermined user input at the computer system:
      automatically generating a second radiographic chest image by globally processing the first projection radiographic chest image using a global presentation to improve the detectability of the PICC;
      automatically electronically linking the second radiographic chest image to the first projection radiographic chest image;
      automatically displaying the second radiographic chest image on the display; and
      automatically displaying an icon on or near the second radiographic chest image to indicate an existence of the electronic linking between the first projection radiographic chest image and the second radiographic chest image, and configuring the icon as an executable link to access and display the first projection radiographic chest image when the icon is selected by an operator.

13. The method of claim 12, wherein the step of automatically displaying an icon on or near the second radiographic chest image comprises displaying a representation of the first projection radiographic chest image on or near the second radiographic chest image.

14. The method of claim 12, wherein the step of automatically displaying an icon on or near the second radiographic chest image comprises displaying a text or symbol on or near the second radiographic chest image.

15. A method for presenting a projection radiographic image of a subject, the method executed at on a computer system, the method comprising:
   displaying, on a display, a first projection radiographic chest image of the subject, wherein content of the first projection radiographic chest image comprises a Peripherally Inserted Central Catheter (PICC);
   automatically generating a second radiographic chest image by globally processing the first projection radiographic chest image using a global presentation to enhance an image quality of the PICC content;
   automatically electronically linking the second radiographic chest image to the first projection radiographic chest image;
   automatically displaying on the display a thumbnail image of the second radiographic chest image while displaying the first projection radiographic chest image; and
   automatically displaying an icon on or near the second radiographic chest image to indicate an existence of the electronic linking between the first projection radiographic chest image and the second radiographic chest image, and configuring the icon as an executable link to access and display the first projection radiographic chest image when the icon is selected by an operator.

16. The method of claim 15, wherein the step of automatically displaying an icon on or near the second radiographic chest image comprises displaying a representation of the first projection radiographic chest image on or near the second radiographic chest image.

17. The method of claim 15, wherein the step of automatically displaying an icon on or near the second radiographic chest image comprises displaying a text or symbol on or near the second radiographic chest image.

18. A method for presenting a projection radiographic image of a subject, the method executed on a computer system, the method comprising:

displaying, on a display, a first projection radiographic chest image of the subject, wherein content of the first projection radiographic chest image comprises a Peripherally Inserted Central Catheter (PICC);

automatically generating a second radiographic chest image by globally processing the first projection radiographic chest image using a global presentation optimized solely to enhance an image quality of both PICC and tube content;

automatically electronically linking the second radiographic chest image to the first projection radiographic chest image;

automatically displaying on the display a thumbnail image of the second radiographic chest image while displaying the first projection radiographic chest image; and automatically displaying an icon on or near the second radiographic chest image to indicate an existence of the electronic linking between the first projection radiographic chest image and the second radiographic chest image, and configuring the icon as an executable link to access and display the first projection radiographic chest image when the icon is selected by an operator.

19. The method of claim 18, wherein the step of automatically displaying an icon on or near the second radiographic chest image comprises displaying a representation of the first projection radiographic chest image on or near the second radiographic chest image.

20. The method of claim 18, wherein the step of automatically displaying an icon on or near the second radiographic chest image comprises displaying a text or symbol on or near the second radiographic chest image.

* * * * *